United States Patent [19]

Coleman

[11] Patent Number: 4,762,649

[45] Date of Patent: Aug. 9, 1988

[54] POLYMERIC ALKYLENE DIPHOSPHONATE ANHYDRIDES, THEIR PRODUCTION AND USE

[75] Inventor: James P. Coleman, Maryland Heights, Mo.

[73] Assignee: Monsanto Company, St. Louis, Mo.

[21] Appl. No.: 9,435

[22] Filed: Feb. 2, 1987

Related U.S. Application Data

[62] Division of Ser. No. 766,724, Aug. 19, 1985, Pat. No. 4,663,432.

[51] Int. Cl.$^4$ ................................................ C07F 9/30
[52] U.S. Cl. ......................... 260/545 P; 260/502.4 P
[58] Field of Search ..................... 260/545 P, 502.4 P

[56] References Cited

U.S. PATENT DOCUMENTS

3,585,166  6/1971  Kerst ............................... 260/545 P
4,195,035  3/1980  Kleiner et al. .................. 260/545 P
4,267,125  5/1981  Dursch et al. ................... 260/545 P

OTHER PUBLICATIONS

Kirk–Othmer Encyclopedia of Chemical Technology, 2nd Ed. (1968), vol. 15, pp. 264–266.
Nweke, Soguzie et al, J. Inorg. Chem., vol. 16 (1977), pp. 860–863.

*Primary Examiner*—Paul J. Killos
*Attorney, Agent, or Firm*—R. Loyer; A. Cole

[57] ABSTRACT

Polymeric phosphonate anhydrides are formed by dehydrating a reaction mixture comprising a salt of a diphosphonic acid. The invention includes the polymeric phosphonate, its method of preparation, and a primary use.

6 Claims, No Drawings

POLYMERIC ALKYLENE DIPHOSPHONATE ANHYDRIDES, THEIR PRODUCTION AND USE

This is a division of application Ser. No. 766,724, filed Aug. 19, 1985 now U.S. Pat. No. 4,663,432.

FIELD OF THE INVENTION

This invention relates to polymeric alkylene diphosphonate anhydrides, their production, and their use in water treatment applications.

BACKGROUND

Phosphonic acid compounds, and their salts, are well known water treatment chemicals. Various phosphonates are used as sequestering agents, scale inhibitors, corrosion inhibitors and additives for use generally in water treatment applications, such as in circulating water systems. Particularly useful are polyphosphonates. Among the most common commercially available polyphosphonates are amino(methylenephosphonic acids) such as amino tri(methylenephosphonic acid), ethylenediamine tetra(methylenephosphonic acid), and others; and hydroxy-phosphonates such ethane-1-hydroxy-1,1-diphosphonic acid. Many additional phosphonates are known in the literature, including unsubstituted alkane diphosphonates, such as 1,2-ethane diphosphonates, whose use for corrosion inhibition is disclosed in U.S. Pat. No. 4,209,487, which is incorporated herein by reference.

Phosphonate condensation polymers have been produced from the reaction of a phosphonic acid group with an alcohol or with an amine having a reactive hydrogen. A polymeric product can be produced by reacting a polyphosphonate or an anhydride of a polyphosphonate with a polyhydric alcohol as is described in U.S. Pat. No. 3,395,113 and U.S. Pat. No. 3,470,112, or by reacting a hydroxyphosphonate such as ethane-1-hydroxy-1,1-diphosphonic acid, as is described in U.S. Pat. No. 3,621,081, in each case forming a polyester. A polymeric product can also be formed by reacting a polyphosphonate anhydride with a polyamine as is described in U.S. Pat. No. 3,645,919. Formation of these polymeric products requires the presence of a reactive hydrogen on either an alcohol or an amine group.

Polymeric bisphosphinic acid anhydrides are described in U.S. Pat. No. 4,196,141, although the degree of polymerization is not specified. These bisphosphinic acid anhydrides are prepared by reacting salts or esters of the bisphosphinates with inorganic acid chlorides, phosgene, oxalyl chloride, the corresponding bromine compounds, or mixtures thereof, at a molar ratio of about 1:1. These bisphosphinate anhydrides are said to be useful as comonomers in the preparation of plastics, particularly polyesters, and for preparation of flame proofing agents. There is no discussion of water treatment uses.

Each of the phosphonates used in water treatment has its individual drawbacks. For instance, aminophosphonates and hydroxyphosphonates are efficient inhibitors of calcium carbonate scale, but are unstable in the presence of oxidants, such as chlorine. Alkylene diphosphonates, such as ethane-1,2-diphosphonic acid, are stable to chlorine, but are relatively inefficient calcium scale inhibitors.

Phosphates are generally better corrosion inhibitors than phosphonates, when used in circulating water systems. However, the formation of calcium phosphate scale can be a problem, because of the presence of calcium ions. This scale formation removes some phosphate from solution, reducing the amount available for corrosion inhibition, and also forms undesirable deposits.

A phosphonate with an improved mix of scale inhibition, corrosion inhibition, and chlorine stability properties would be a significant advance in the art and is an object of this invention.

SUMMARY OF THE INVENTION

This invention provides a polymeric phosphonate anhydride with an average molecular weight at least about 1000, formed by dehydrating a reaction mixture comprising a salt of a diphosphonic acid of the formula:

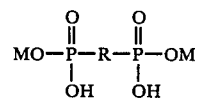

where M is an alkali metal and R is an unsubstituted alkylene group, preferably a C1 to C4 alkylene group.

The reaction mixture may optionally contain a phosphate, preferably an orthophosphate, along with the diphosphonic acid salt, in a mole ratio of phosphate to phosphonate from 0 to about 5.

The polymer so produced is believed to have the following structure:

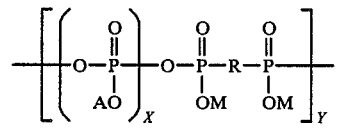

where R and M are as defined above, A is either hydrogen or an alkali metal, X averages from 0 to about 5, and Y is an integer of at least 5.

This invention also provides a process for producing a polymeric phosphonate anhydride by heating, from about 200° C. to about 400° C., under an inert atmosphere, a salt of a diphosphonic acid of the following formula:

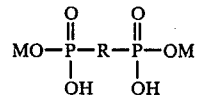

where M and R are as defined above, optionally along with a phosphate, preferably an orthophosphate.

This invention also provides a method for inhibiting formation of scale in an aqueous solution containing scale forming ions, by incorporating into the aqueous solution an effective amount of a polymeric phosphonate anhydride of the following formula:

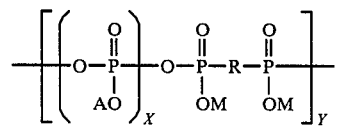

where M is an alkali metal, R is an unsubstituted alkylene group, A is hydrogen, an alkali metal or an ammonium group, X averages from 0 to about 5 and Y is an integer of at least about 5.

This method is particularly effective at inhibiting the formation of calcium carbonate scale. The amount of the polymeric phosphonate anhydride needed to be effective at inhibiting scale formation depends upon the conditions present, such as pH, temperature, concentrations, etc. However, it is preferred that the inhibitor be present in at least about 1 ppm, more preferably at least about 5 ppm.

DESCRIPTION OF THE INVENTION

The polymeric phosphonate anhydrides of this invention can be prepared from diphosphonic acid salts having the following formula:

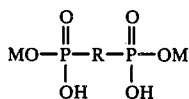

where M is either an alkali metal and where R is an alkylene group. It is preferred that M is an alkali metal, and due to cost and availability, it is particularly preferred that M is sodium. The alkylene group is preferably C1 to C6 and more preferably C1 to C4. The alkylene group is unsubstituted. As used herein unsubstituted means that the alkylene group does not contain any group which readily reacts with the phosphonate group. The alkylene group may be either straight chain or branched. The preferred alkylene groups are $\alpha,\omega$-alkylene groups, more preferably 1,2-ethylene.

Examples of suitable diphosphonic acid salts include disodium ethane-1,2-diphosphonic acid; disodium propane-1,3-diphosphonic acid, disodium methane diphosphonic acid.

These diphosphonic acid salts can be prepared by partial neutralization of the corresponding diphosphonic acid. The diphosphonic acids can be prepared by known methods, such as by addition of orthophosphorous acid across an olefinic or acetylenic bond, for example, by photoinitiation, as is described in U.S. Pat. No. 2,957,931, which is incorporated herein by reference; by hydrogenolysis of hydroxyalkyl diphosphonic acid; or by other methods known to one skilled in the art.

In addition to the salt of the diphosphonic acid, discussed above, the reaction mixture to be dehydrated can also contain a phosphate. Any phosphate which condenses with the diphosphonic acid salt can be used. Examples are orthophosphates, pyrophosphates, and polyphosphates, with orthophosphates being preferred, more preferably monosodium orthophosphate. The mole ratio of phosphate to diphosphonic acid salt may range from 0 to about 5, preferably from 0 to about 2.

Normally no solvent, dehydrating agent, or other additives are necessary, however there are some circumstances in which they may advantageously be used.

The polymeric anhydride can be prepared by heating the diphosphonic acid salt, together with any optional phosphate under an inert atmosphere. The dehydration temperature is preferably from about 200° C. to about 400° C., more preferably from about 290° C. to about 350° C. The diphosphonic acid salt is maintained within the desired temperature range until the desired molecular weight has been attained, preferably at least about 6 hours, more preferably from about 1 hour to about 3 hours. If the polymeric phosphonate anhydride is intended for use as a water solution, the molecular weight should not be allowed to reach a point where solubility is below the level required for the intended application. Any atmosphere that does not react with the diphosphonate salt or any phosphate present, can be used, with dry nitrogen being preferred. The atmosphere may be dried during dehydration to remove water liberated by the dehydration reaction, such as by circulating through a dessicant or a cold trap, or by any means known to one skilled in the art. Some means of mixing the mixture being dehydrated can advantageously be used in some circumstances, although it is not essential. The reaction may also be run under vacuum in order to remove water even more rapidly.

The polymeric phosphonate anhydride can be recovered by conventional means. If the reaction mixture contains only the diphosphonate salt and phosphate, no separation is necessary. If solvents, dehydrating agents, or other substances are also included, some separation may be required.

The polymeric phosphonate anhydrides of this invention are useful for a variety of water treatment applications. They are substantially better calcium carbonate scale inhibitors than the corresponding diphosphonate salt precursors, and are active in threshold amounts, e.g. in less than stoichiometric amounts compared with the calcium carbonate present. They are substantially more stable in the presence of chlorine, or other oxidants than aminophosphonates or hydroxyphosphonates.

These polymeric phosphonate anhydrides are also active as corrosion inhibitors, in aqueous systems, particularly in the presence of a small amount of a phosphate, such as orthophosphate. Because these polymeric phosphonate anhydrides do not hydrolyze directly to produce orthophosphates, as condensed phosphates do, use of these polymeric phosphonate anhydrides can help to reduce the amount of orthophosphate present in the system. This is important because orthophosphate can combine with calcium ions to form calcium orthophosphate scale. The inhibition of calcium orthophosphate scale has proven to be relatively difficult.

Additionally, because of their structure, these polymeric phosphonate anhydrides, would be expected to be active as sequestrants, dispersants, and in other water treatment applications.

The following Examples are intended to illustrate this invention and are not intended in any way to limit its scope. The ethane-1,2-diphosphonic acid (EDPA) was prepared by photoinitiated reaction of acetylene with aqueous phosphorous acid, in the presence of acetone.

The product was an aqueous solution with a phosphonate content consisting of 77% by weight EDPA and 23% phosphorous acid, which will be referred to herein as "crude EDPA". This crude EDPA was purified by filtration and acetone washing to produce a product that was 98% EDPA and 2% phosphorous acid, which will be referred to herein as "refined EDPA". The refined EDPA was partially neutralized with sodium hydroxide, to produce disodium EDPA.

EXAMPLE 1

Disodium EDPA, prepared as described above, was heated, under a nitrogen atmosphere, to the indicated temperature, and was maintained at this temperature for the indicated time. Some of the samples also contained monosodium orthophosphate at the indicated mole ratio with the disodium EDPA. A polymeric alkylene diphosphonate anhydride resulted. The polymeric anhydride was either a "homopolymer" of the disodium EDPA, or a "copolymer" of the phosphate and the disodium EDPA. The weight average molecular weight of each sample was determined by Gel Permeation Chromatography-Low Angle Laser Light Scattering. The results are shown in Table 1.

TABLE 1

| Sample No. | Mole Ratio PO4: EDPA | Temp. | Time | Polymer Produced | Molecular Weight |
|---|---|---|---|---|---|
| 1 | 0:1 | 350° C. | 2½ hrs. | (Na2EDPA) | 5,200 |
| 2 | 0:1 | 290° C. | 5 hrs. | (Na2EDPA) | 18,700 |
| 3 | 1:1 | 350° C. | 3 hrs. | [(EDPA + PO4)Na3] | 1,800 |
| 4 | 2:1 | 350° C. | 3 hrs. | [(EDPA + 2PO4)Na4] | 6,500 |
| 5 | 1:1 | 350° C. | 3 hrs. | [(EDPA + PO4)Na4]* | 1,600 |

*An excess of NAOH in the sample may have caused a different or impure structure.

EXAMPLE 2

Calcium carbonate scale inhibition at various dosages was determined for all Samples from Example 1 and for crude EDPA and refined EDPA according to the following procedure:

A solution was made up with 645 ppm of calcium, 280 ppm of sodium carbonate, and 1110 ppm of sodium bicarbonate, which results in a solution with approximately stoichiometric amounts of calcium and carbonate in sufficient quantity to be expressed as 1600 ppm of calcium carbonate. The pH was adjusted to 8.6. The indicated amount of inhibitor was added as the sodium salt and the solutions were swirled for 24 hours at 25° C. The solutions were then filtered and the amount of calcium remaining in solution was determined by titrating with EDTA. The % scale inhibition was calculated as follows:

$$\% \text{ Inhib} = \frac{\text{ppm CaCO}_3(\text{sample}) - \text{ppm CaCO}_3(\text{control})}{\text{ppm CaCO}_3(\text{initial}) - \text{ppm CaCO}_3(\text{control})} \times 100$$

The results are shown in Table 2.

TABLE 2

| | Calcium Carbonate Scale Inhibition, %, vs. Dosage | | | |
|---|---|---|---|---|
| Sample No. | 2 ppm | 5 ppm | 10 ppm | 25 ppm |
| Crude EDPA | — | 19% | 23% | 97% |
| Refined EDPA | — | 8% | 12% | 27% |
| Sample 1 | 25% | 48% | 100% | 100% |
| Sample 2 | 46% | 72% | 100% | 100% |
| Sample 3 | 37% | 96% | 100% | 100% |
| Sample 4 | 34% | 66% | 100% | 100% |
| Sample 5 | 40% | 98% | 98% | 98% |

The data in Table 2 demonstrate that these polymeric diphosphonate anhydrides are effective inhibitors of calcium carbonate scale at a much lower dose level than the EDPA.

EXAMPLE 3

Corrosion inhibition for carbon steel was determined by immersing a coupon of carbon steel in 4X Pittsburgh water, with 1000 ppm chloride. This coupon and water were maintained at 75° C. for one week. Rate of corrosion was determined by weight loss of the coupon, and was expressed in mils per year, mpy. Corrosion rate was determined at the indicated dosages of Sample 1 of the polymeric diphosphonate anhydride, of Sample 1 with orthophosphonate, crude EDPA, and refined EDPA. The results are shown in Table 3.

TABLE 3

| Dosage | Corrosion Rate (mpy) |
|---|---|
| 0 | 17 |
| 10 ppm Sample 1 | 8.06 |
| 20 ppm Sample 1 | 7.53 |
| 50 ppm Sample 1 | 2.94 |
| 25 ppm Sample 1 + 10 ppm PO4 | 1.11 |
| 50 ppm Crude EDPA | 2.3 |
| 50 ppm Refined EDPA | 4.7 |

The data in Table 3 demonstrate that these polymeric diphosphonate anhydrides are active as corrosion inhibitors, either when used above, or when used along with a phosphate.

These Examples are illustrative only and are not intended in any way to limit the scope of this invention. One skilled in the art will recognize many variations and alternatives within the spirit and scope of this invention.

I claim:

1. A method for preparing a polymeric phosphonate comprising heating from about 200° C. to about 400° C., under an inert atmosphere, a reaction mixture comprising a salt of a diphosphonic acid of the formula:

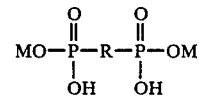

where M is an alkali metal and where R is an unsubstituted alkylene group having 2 to 6 carbon atoms.

2. A method of claim 1 wherein the temperature is in the range of from about 290° C. to about 350° C.

3. A method of claim 1 wherein the heating is continued for a period of from about 1 hour to about 3 hours.

4. A method of claim 1 wherein the inert atmosphere is nitrogen.

5. A method of claim 1 wherein the salt of the diphosphonic acid is disodium propane-1,3-diphosphonic acid.

6. A method of claim 1 wherein the salt of the diphosphonic acid is disodium ethane diphosphonic acid.

* * * * *